United States Patent [19]

Menard et al.

[11] 4,155,912

[45] May 22, 1979

[54] 2-METHYLPENEM-3-CARBOXYLIC ACID ANTIBIOTICS

[75] Inventors: Marcel Menard, Candiac; Gilles Caron, Brossard, both of Canada

[73] Assignee: Bristol-Myers Company, New York, N.Y.

[21] Appl. No.: 860,351

[22] Filed: Dec. 14, 1977

[51] Int. Cl.² .................................... C07D 277/60
[52] U.S. Cl. .................... 260/306.7 C; 424/270; 260/239 A
[58] Field of Search .................. 260/306.7 C

[56] References Cited

U.S. PATENT DOCUMENTS 3,950,357    4/1976    Kahan et al. .................. 260/326.27

FOREIGN PATENT DOCUMENTS 846933  10/1976  Belgium.
849118   6/1977  Belgium.
1467413  3/1977  United Kingdom.

OTHER PUBLICATIONS

Brown et al., JCS Chem. Comm., 359;14 360, (1977).

Primary Examiner—Nicholas S. Rizzo
Attorney, Agent, or Firm—David M. Morse

[57] ABSTRACT

There is described the preparation of novel 2-penem-3-carboxylic acid compounds having the formula

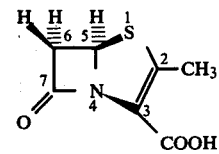

I and easily cleavable esters and carboxylic acid salts thereof. The compounds of formula I, particularly the dextrorotatory isomers thereof, are potent antibacterial agents or are of use as intermediates in the preparation of such agents.

17 Claims, No Drawings

2-METHYLPENEM-3-CARBOXYLIC ACID ANTIBIOTICS

BACKGROUND OF THE INVENTION

1. Field of the Invention

The chemical processes of the present invention provide novel antibacterial agents of the β-lactam type containing a hitherto unknown nucleus and useful intermediates for the synthesis of said antibacterial agents.

2. Description of the Prior Art

Penicillins and cephalosporins comprise a group of well-known antibacterial agents commonly grouped together as a class called β-lactam antibiotics. Most of the work in this field has been done, broadly speaking, with 6-aminopenicillanic acid, 7-aminocephalosporanic acid and derivatives thereof produced by fermentation or chemical transformation of the natural products. Despite the extensive progress made in preparing active derivatives of 6-aminopenicillanic acid and 7-aminocephalosporanic acid, there is a continuing search for synthetic and semisynthetic routes to new families of β-lactam antibiotics which may possess more advantageous properties than those derived from the known penicillin and cephalosporin nuclei.

Literature publications relating to other more non-conventional β-lactam-containing antibiotics include the following:

a. Belgian Patent 846,933 discloses the compound of the formula

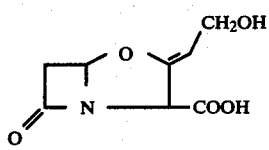

which has been isolated from fermentation of *Streptomyces clavuligerus*. This compound, named clavulinic acid, possesses a low order of antibacterial activity but inhibits the action of certain β-lactamases and reportedly enhances the in vitro and in vivo activity of some penicillins and cephalosporins.

b. U.K. Patent No. 1,467,413 discloses the fermentation product having the formula

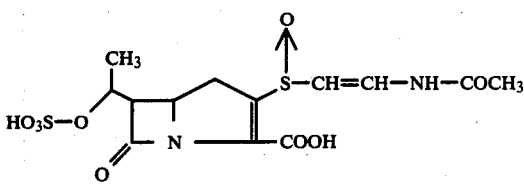

which is reported to possess some antibacterial activity and to be a β-lactamase inhibitor.

c. Brown, et al. in J.C.S. Chem. Comm., 359–360 (1977) disclose preparation of the compound of the formula

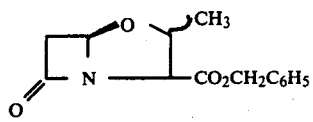

There is no indication from the publication that the compound possesses any antibacterial activity.

d. U.S. Pat. No. 3,950,357 describes a fermentation process for producing thienamycin, the compound of the formula

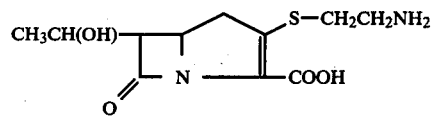

Thienamycin is reported to be a highly potent broad-spectrum antibiotic.

e. Belgian Patent No. 849,118 discloses a series of 6-amino-2-penem-3-carboxylic acid derivatives of the formula

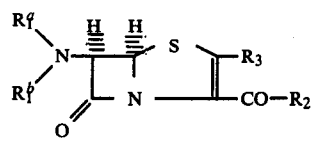

where $R_1{}^a$ is hydrogen or an N-protecting group, $R_1{}^b$ is hydrogen or acyl (or $R_1{}^a$ and $R_1{}^b$ taken together are a divalent N-protecting group), $-CO-R_2$ is carboxyl or a protected carboxyl group and $R_3$ is hydrogen or a C-bonded organic group. The compounds and their salts are said to possess antibacterial activity. Example 8 in the Belgian Patent discloses the compound where $R_1{}^a$ is hydrogen, $R_1{}^b$ is $C_6H_5OCH_2CO-$, $R_2$ is OH and $R_3$ is $CH_3$. No compounds are disclosed in the publication which do not contain the amino or acylamido moiety at the 6-position of the β-lactam ring.

SUMMARY OF THE INVENTION

The present invention provides a novel β-lactam compound having the formula

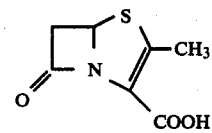

I or a pharmaceutically acceptable salt or easily cleavable ester thereof. The above compounds, including especially the dextrorotatory optical isomers thereof, are potent antibacterial agents or are intermediates useful in preparing said antibacterial agents.

Also included in this invention are various novel intermediates useful in preparing the active β-lactam derivatives described above and processes for the production of the intermediates and active compounds.

The compounds represented by formula I form a new β-lactam ring system. The nomenclature to be used for the compounds could be the following:

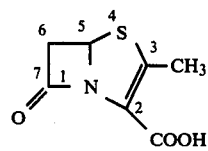

3-methyl-7-oxo-4-thia-1-azabicyclo[3,2,0]hept-2-ene-2-carboxylic acid.

Alternatively, the compounds can be considered as penem derivatives and named as follows:

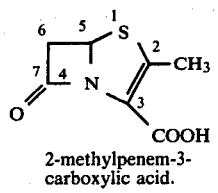

2-methylpenem-3-
carboxylic acid.

The stereoconfiguration of the 2-penem compounds of the present invention may be represented as follows:

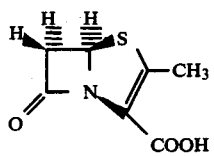

Since an asymmetric carbon atom is present (carbon 5 of the penem ring), the compounds of formula I may exist either in the form of racemic mixtures or as the individual dextrorotatory and levorotatory optical isomers. While the present invention includes both the racemic mixtures and resolved optical isomers, the preferred compounds are the dextrorotatory optical isomers (S-configuration) since these have been found to possess substantially all of the antibacterial activity attributed to the racemic mixtures.

The pharmaceutically acceptable salts referred to above include nontoxic metallic salts such as sodium, potassium, calcium and aluminum, the ammonium salts and salts with nontoxic amines such as trialkylamines (e.g. triethylamine), procaine, dibenzylamine, N-benzyl-β-phenethylamine, 1-ephenamine, N,N'-dibenzylethylenediamine, N-alkylpiperidine (e.g. N-ethylpiperidine), α-methylbenzylamine, α-ethylbenzylamine, and other amines which have been used to form salts of penicillins and cephalosporins.

Easily cleavable esters of the free acid compounds of formula I include conventional ester groups which have been used in the penicillin and cephalosporin art to block carboxyl groups, i.e. ester groups which are removable by methods which do not result in any appreciable destruction of the remaining portion of the molecule. For use as an intermediate, the preferred easily cleavable ester is the p-nitrobenzyl ester which may be removed by hydrogenolysis, e.g. catalytic hydrogenation with a noble metal catalyst. For use as biologically active compounds, physiologically cleavable esters are employed. Physiologically cleavable esters of the free acid compounds of formula I include those esters known in the penicillin and cephalosporin art to be easily cleaved within the body to the parent acid. Examples of such esters include indanyl, phthalidyl, methoxymethyl, glycyloxymethyl, phenylglycyloxymethyl, thienylglycyloxymethyl or acyloxymethyl of the formula

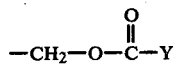

in which Y is $C_1-C_4$ alkyl or phenyl. Particularly preferred biologically active esters are methoxymethyl, acetoxymethyl, pivaloyloxymethyl, phthalidyl and indanyl.

It will be appreciated that the compounds of formula I may exist in various states of solvation and the anhydrous as well as solvated forms are intended to be within the scope of the invention.

The present invention further provides various novel intermediates useful in the synthesis of the compounds of formula I.

A preferred embodiment of the present invention is a novel intermediate of the formula

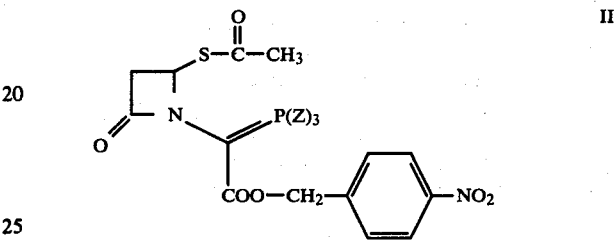

wherein Z is phenyl or $C_1-C_6$ alkyl (e.g. n-butyl). The most preferred compound of formula II is that in which Z is phenyl.

Another preferred embodiment of the present invention is a novel intermediate of the formula

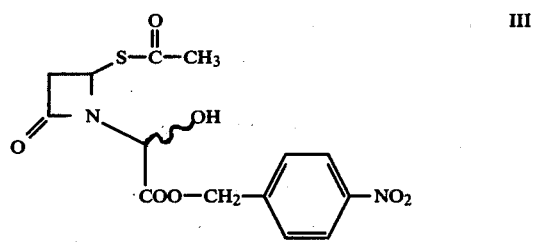

wherein the wavy line indicates that compound III exists as a mixture of epimers.

Another preferred embodiment of the present invention is a novel intermediate of the formula

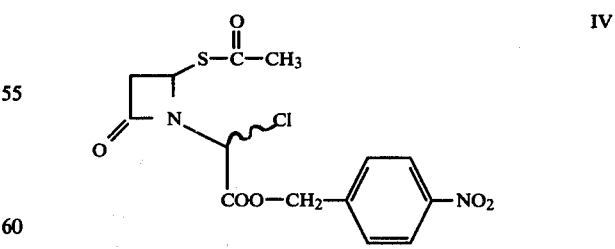

which exists in the form of a mixture of epimers.

The 2-penem compounds of formula I may be prepared by the process comprising the steps of (1) thermally cyclizing in an inert organic solvent a phosphorane intermediate of the formula

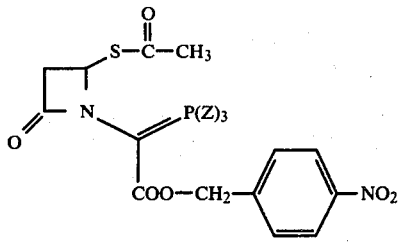

wherein Z represents phenyl or $C_1$–$C_6$ alkyl but preferably phenyl to produce a compound of the formula

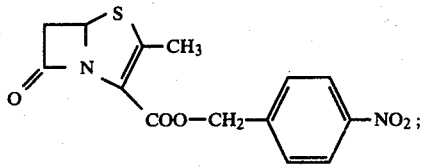

(2) subjecting the ester of formula $I_a$ to catalytic hydrogenation employing a noble metal catalyst in a non-reducible inert aqueous or non-aqueous solvent in the presence or absence of a base to produce the racemic acid of the formula

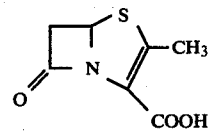

or a carboxylic acid salt thereof and, if desired, performing one or more of the further steps selected from (a) resolving the so-produced racemic compound into its dextrorotatory and levorotatory optical isomers thereof and recovering the dextrorotatory isomer; and (b) converting the racemic free acid or salt of formula I or the dextrorotatory isomer thereof to a physiologically hydrolyzed ester thereof or a pharmaceutically acceptable carboxylic acid salt thereof.

The cyclization reaction may be carried out in an inert organic solvent or mixture of solvents such as aliphatic, cycloaliphatic or aromatic hydrocarbons (e.g. n-hexane, cyclohexane, benzene or toluene), halogenated hydrocarbons (e.g. methylene chloride, chloroform, carbon tetrachloride), ethers (e.g. diethyl ether, dioxane or tetrahydrofuran), carboxylic acid amides (e.g. dimethylformamide), di $C_1$–$C_6$ alkylsulfoxides (e.g. dimethylsulfoxide) or a $C_1$–$C_6$ alkanol (e.g. methanol, ethanol, t-butanol). Elevated temperatures are used, for example, temperatures ranging from above room temperature to the reflux temperature of the solvent system. Good results are obtained at temperatures of from about 50°–100° C.

The p-nitrobenzyl ester $I_a$ is then cleaved by hydrogenolysis in a conventional manner to give the corresponding free acid or a salt thereof. Catalytic hydrogenation may be employed with a noble metal catalyst such as palladium or rhodium, including derivatives thereof such as oxides, hydroxides or halides, said catalyst being optionally supported on a conventional carrier such as carbon or diatomaceous earth. A non-reducible aqueous or non-aqueous inert solvent such as water, methanol, ethanol, ethyl acetate, tetrahydrofuran, diethyl ether or dioxane is used for the hydrogenolysis reaction. The reaction is preferably conducted at atmospheric or slightly elevated pressure at room temperature and for a period of from about 1 to 5 hours depending on the solvent and catalyst used. If an equivalent weight of a base such as an alkali metal or alkaline earth hydroxide or an amine is employed during the hydrogenolysis, the product may be recovered in the form of a carboxylic acid salt. Alternatively, if no base is used, the free acid product is obtained.

Compound I is recovered from the hydrogenolysis step as a racemic mixture of the dextrorotatory and levorotatory optical isomers of the free acid or salt thereof. While the racemic mixture possesses potent antibacterial activity and may be employed in that form as an antibiotic agent, it has been found upon resolution of the racemate that substantially all of the antibacterial activity is in the dextrorotatory optical isomer. Accordingly, it is preferred to resolve the racemic compound I into its optical isomers by a conventional resolution procedure, e.g. by reacting the racemic acid with an optically active amine such as α-methylbenzylamine to form diastereoisomeric salts, separating the salts and converting them into the dextrorotary and levorotatory optical isomers of free acid I. By this procedure the dextrorotatory isomer may be recovered in a form substantially free of the less active levorotatory isomer.

A racemic or resolved compound of formula I may then be converted to a pharmaceutically acceptable salt thereof or a physiologically cleavable ester thereof. Pharmaceutically acceptable salts may be formed by reaction of the acid of formula I with a suitable non-toxic base in an inert solvent and recovering the desired salt as by precipitation or lyophilization. Physiologically cleavable esters may be prepared from the racemic or resolved free acids or salts in an analogous manner to preparation of such esters of penicillins and cephalosporins.

Acyloxymethyl esters in which the 3-position of the 2-penem has the formula

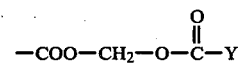

in which Y is phenyl or $C_1$–$C_4$ alkyl may be prepared by reacting an alkali metal salt of the free acid I (in the form of the racemic mixture or resolved dextrorotatory isomer), for example, the lithium, sodium or potassium salt, with an acyloxymethyl halide of the formula

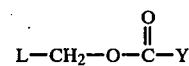

in which L is chloro or bromo and Y is $C_1$–$C_4$ alkyl or phenyl. Acyloxymethyl halides which may be employed include chloromethyl acetate, bromomethyl acetate, bromomethyl propionate, chloromethyl pivaloate, chloromethyl benzoate, and the like. The alkali metal salt of compound I is reacted in an inert solvent (e.g. tetrahydrofuran, dioxane, dimethylformamide or methylene chloride) with at least a molar equivalent of the acyloxymethyl halide at room temperature or at slightly elevated temperature, e.g. up to ~40°–45° C.

The methoxymethyl ester of compound I (racemic mixture or dextrorotatory isomer) wherein the 3-position is —COO—$CH_2OCH_3$ may be prepared by substituting for the acyloxymethyl halide in the above procedure chloromethyl methyl ether.

The indanyl ester of compound I wherein the 3-position has the formula

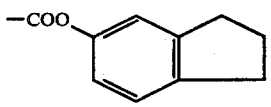

may be prepared by reacting 5-indanol in an inert solvent such as dioxane or tetrahydrofuran with the free acid form of compound I (racemic mixture or dextrorotatory isomer) in the presence of a condensing agent such as N,N'-dicyclohexylcarbodiimide.

Phthalidyl ester compounds of formula I where the 3-position has the formula

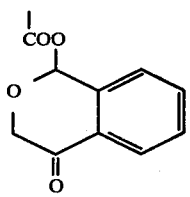

may be prepared by reacting bromophthalide having the formula

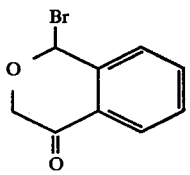

with a salt of the free acid I (racemic mixture or dextrorotatory isomer). The esterification can be carried out in an inert solvent such as dimethylformamide, dioxane or tetrahydrofuran by warming equimolar amounts of the salt of formula I, for example, the sodium or potassium salt, and bromophthalide.

The phosphorane intermediate of formula II may be prepared from 4-acetylthio-2-azetidinone, a known compound, by the following procedure:

(a) reacting 4-acetylthio-2-acetidinone of the formula

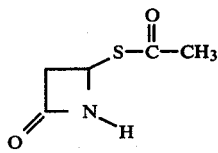

with a glyoxylic acid ester of the formula

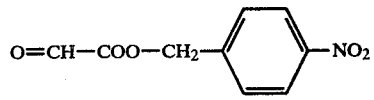

or a reactive oxo-derivative thereof such as a hydrate in an inert organic solvent, preferably at an elevated temperature, to produce a mixture of epimers having the formula

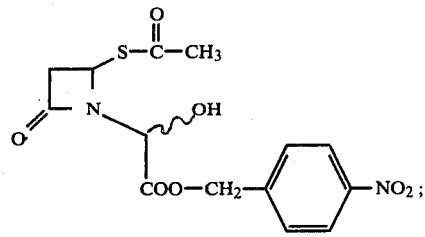

(b) converting the so-produced hydroxy intermediate III to the corresponding chloro epimeric mixture of the formula

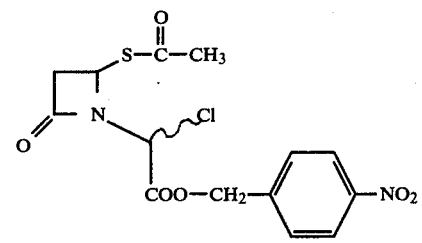

by treatment with a chlorinating agent in an inert organic solvent in the presence or absence of a base;

(c) reacting the chloro intermediate IV with a phosphine compound of the formula

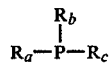

where $R_a$, $R_b$ and $R_c$ are phenyl or $C_1$-$C_6$ alkyl, preferably phenyl, in an inert organic solvent in the presence of a base to produce the desired phosphorane intermediate II.

Reaction step (a) is carried out in a suitable inert organic solvent such as benzene or toluene with p-nitrobenzyl glyoxylate or a reactive oxo-derivative thereof such as p-nitrobenzyl glyoxylate hydrate. The reaction is preferably carried out at elevated temperatures (e.g. 50°-150° C.), most preferably under reflux conditions. When a hydrate of the ester is used, resulting water may be removed azeotropically or with molecular sieves. The hydroxy ester product III is formed as a mixture of epimers which may be optionally purified by chromatography or used directly in the next step.

The chloro ester intermediate IV is next formed by reacting intermediate III in an inert organic solvent (e.g. tetrahydrofuran, dioxane or a mixture thereof) in the presence or absence of a base, preferably an organic base such as an aliphatic tertiary amine (e.g. triethylamine) or a heterocyclic tertiary amine (e.g. pyridine or collidine), with a chlorinating agent capable of converting a hydroxy group to a chloro group such as $SOCl_2$, $POCl_3$ or $PCl_5$. Preferred temperatures for this step are room temperature for the case when a base is not employed to about 0° to −10° C. when a base is present. The product IV is again obtained as a mixture of epimers which can optionally be purified by chromatography before use in step (c).

Intermediate IV is converted to the phosphorane intermediate II by reaction with triphenylphosphine or a tri(lower)alkylphosphine such as tri-n-butylphosphine in an organic solvent (e.g. an aliphatic, cycloaliphatic or aromatic hydrocarbon such as hexane, cyclohexane, benzene or toluene or an ether such as dioxane or tetrahydrofuran, or a mixture thereof) in the presence of a base, preferably an organic tertiary amine such as triethylamine, pyridine or 2,6-lutidine. The reaction may be carried out at temperatures from room temperature up to the reflux temperature of the solvent system. Intermediate II may be optionally purified by chromatography before being used as the starting material for preparation of compound I.

The free acid compound of formula I in the form of the racemic mixture or resolved dextrorotatory optical isomer and pharmaceutically acceptable salts and physiologically cleavable esters of said acid have been found to be potent broad-spectrum antibacterial agents useful in the treatment of infectious diseases in animals, including man, caused by both Gram-positive and Gram-negative organisms. The compounds are also of value as nutritional supplements in animal feeds and as agents for the treatment of mastitis in cattle. In addition, the active compounds of the invention possess good β-lactamase resistance and show advantageously high blood serum levels upon oral or parenteral administration.

The active compounds provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered orally or parenterally in an amount of from about 5 to 200 mg./kg./day and preferably about 5 to 20 mg./kg./day in divided dosage, e.g. three or four times a day. They are administered in dosage units containing, for example, 125, 250 or 500 mg. of active ingredient with suitable physiologically acceptable carriers or diluents.

The present invention also provides a method of combatting bacterial infections in animals, particularly warm-blooded animals, which comprises administering an acid of formula I or a physiologically cleavable ester thereof or a pharmaceutically acceptable salt thereof, either in the form of a racemic mixture or preferably a dextrorotatory isomer, or a pharmaceutical composition thereof, to an infected host in an amount sufficient to combat such infection.

Illustrative examples of the preparation of starting materials and compounds of the present invention follow. These examples are given in illustration of, but not in limitation of, the present invention. All temperatures are in degrees Celsius. Unless otherwise indicated, the products of Examples 1-8 are racemic mixtures.

PREPARATION OF STARTING MATERIALS

Preparation 1: 4-Acetylthio-2-azetidinone

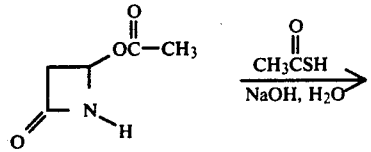

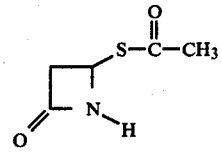

To a cold (0°-5° C.) oxygen-free 1 N NaOH solution (27.5 ml.) was added thioacetic acid (2.09 g., 27.5 mmole) at such a rate that the temperature was maintained between 0°-5° C. The resulting solution was added dropwise (over 20 min.) to a cold (0.5° C.) oxygen-free aqueous solution (11 ml.) of 4-acetoxy-2-azetidinone (3.23 g., 25 mmole) [prepared in *Liebigs Ann. Chem.*, 539 (1974)]. The reaction mixture was stirred under a nitrogen atmosphere for 0.5 hr. at 0°-5° C. and for 2-2.5 hr. at 23°-25° C. before being extracted with chloroform (4×25 ml.). The organic extracts were combined, washed with water (10 ml.), dried over anhydrous $Na_2SO_4$ and concentrated to a yellow syrup, 3.3 g., 91% yield. The title product was found to be identical to the sample prepared by Clauss in *Liebigs Ann. Chem.*, 539 (1974). δ (ppm, $CDCl_3$), 7.2 (1H, NH), 5.23 (1H, dd, $J_{cis}=2.8$, $J_{trans}=5.0$, H-H), 3.55 (1H, ddd, $J_{gem}=15.2$, $J_{HNH}=2.0$, H-3 trans), 2.95 (1H, ddd, $J_{gem}=15.2$, $J_{cis}=2.8$, $J_{HNH}S1$, H-3 cis) and 2.36 (3H, s, methyl).

Preparation 2: 4-Acetylthio-2-azetidinone (Preferred Process)

To a cold (0°-5°) oxygen-free 1 N NaOH solution (803 ml.) was added over 20 minutes thioacetic acid (57 ml., 61 g., 0.803 mole). The resulting solution was added in ca 20 minutes to a cold (10°) oxygen-free solution of 4-acetoxyazetidinone (94 g., 0.730 mole) in water (300 ml.). The pH of the resulting solution was immediately adjusted to 7.4 with solid $NaHCO_3$. The cooling bath was removed and the solution was stirred for 2.75 hours. The mixture was then extracted with chloroform, the combined organic extracts washed with water (150 ml.) and dried over sodium sulfate. Concentration on a rotary evaporator left a yellow oil (95.3 g., 90%) which solidified to a yellow solid on cooling and seeding. This solid was found identical (by IR, NMR and TLC) to the product obtained in Preparation 1.

EXAMPLE 1 p-Nitrobenzyl 2-Methylpenem-3-carboxylate

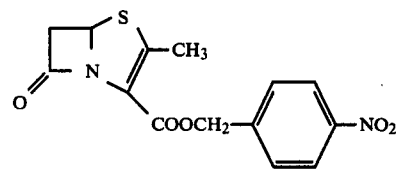

A. Preparation of p-Nitrobenzyl 2-(4-Acetylthio-2-oxo-1-azetidinyl)-2-hydroxyacetate

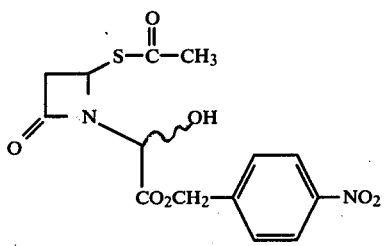

A solution of 4-acetylthio-2-azetidinone (3.33 g., 23 mmole) and p-nitrobenzyl glyoxylate (5.25 g., 25 mmole) in benzene (250 ml.) was heated under reflux for 18 hours. Evaporation of the solvent left an oil which was purified by filtration through a pad of silica gel. There was obtained 8.2 g. (100% yield) of the title intermediate. $R_f=0.8$ (ethyl acetate:CHCl$_3$, 4:1 v/v). δ(ppm, CDCl$_3$): 7.9 (4H, m, aromatic), 5.4 (4H, m, two benzylic H, H-4 and H of glyoxylate), 4.7 (1H, hydroxyl), 3.32 (2H, m, H-3), 2.4 (3H, two s, CH$_3$). $\nu_{c=o}=1775$, 1760, 1695 cm$^{-1}$, mixture of two epimers.

B. Preparation of p-Nitrobenzyl 2-(4-Acetylthio-2-oxo-1-azetidinyl)-2-chloroacetate

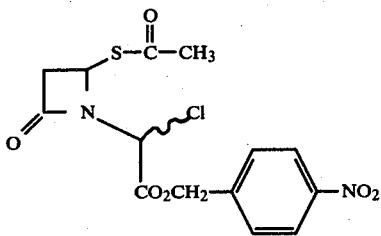

To a cooled (0°) and stirred solution of p-nitrobenzyl 2-(4-acetylthio-2-oxo-1-azetidinyl)-2-hydroxyacetate (3.79 g., 10.7 mmole) in tetrahydrofuran (40 ml.) and dioxane (40 ml.) was added pyridine (0.97 ml., 12 mmole) followed by SOCl$_2$ (1.43 g., 0.88 ml., 12 mmole). The mixture was stirred 30 minutes at 0°, the precipitate was removed and washed with toluene, and the combined filtrates were concentrated on a rotary evaporator to leave a yellow oil. Partial purification was achieved by filtering the residue over a silica gel pad and washing with chloroform. δ(ppm, CDCl$_3$): 8.2 (2H, m, aromatic), 7.55 (2H, m, aromatic), 6.12 (1H, s, CHCl), 5.65 (1H, m, H-4), 5.35 (2H, two s, benzylic H), 3.62 (1H, dd, $J_{3\text{-}3}=16$, $J_{3\text{-}4\ cis}=6$, H-3), 3.08 (1H, m, H-3), 2.35 (3H, two s, CH$_3$). The product was obtained as a mixture of two epimers.

C. Preparation of p-Nitrobenzyl 2-(4-Acetylthio-2-oxo-1-azetidinyl)-2-triphenylphosphoranylideneacetate

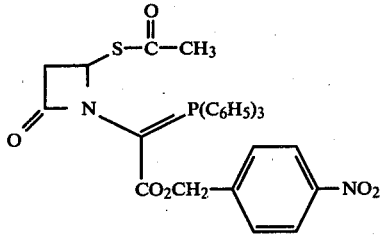

2,6-Lutidine (2.14 g., 20 mmole) was added to a solution of p-nitrobenzyl 2-(4-acetylthio-2-oxo-1-azetidinyl)-2-chloroacetate (5.9 g., 16 mmole) and triphenylphosphine (5.8 g., 22 mmole) in dioxane (80 ml.). The solution was kept at 55° for 18 hours and then concentrated on a rotary evaporator. The residue was partitioned between brine and ethyl acetate and the organic phase was washed with brine, dried and concentrated. The residue was purified by chromatography over silica gel (ethyl acetate:petroleum ether, 1:2 v/v) to give 4.64 g. (48%) of the title ester.

D. Preparation of p-Nitrobenzyl 2-Methylpenem-3-carboxylate

A solution of p-nitrobenzyl 2-(4-acetylthio-2-oxo-1-azetidinyl)-2-triphenylphosphoranylideneacetate (2.4 g., 4.0 mmole) in toluene (35 ml.) was heated under reflux for 4 hours. Chromatography over silica gel afforded 689 mg. (53% yield) of title product as a yellow solid, m.p. 129°–131° C. $R_f=0.7$ (ethyl acetate:petroleum ether, 1:1 v/v). $\nu_{c=o}=1785$, 1710 cm$^{-1}$. δ(ppm, CDCl$_3$): 8.3, 8.17, 7.67, 7.52 (4H, m, aromatic), 5.62 (1H, q, H-5), 5.30 (2H, d, benzylic H), 3.82 (1H, dd, $J_{6\text{-}6}=16$, $J_{5\text{-}6\ cis}=4$, H-6, 3.42 (1H, dd, $J_{6\text{-}6}=16$, $J_{5\text{-}6\ trans}=2$), 2.39 (3H, s, CH$_3$).

EXAMPLE 2 p-Nitrobenzyl 2-Methylpenem-3-carboxylate (Preferred Process)

A. p-Nitrobenzyl 2-(4-acetylthio-2-oxo-1-azetidinyl)-2-hydroxyacetate p-Nitrobenzyl glyoxylate hydrate (63.4 g., 0.278 mole) was added to a solution of 4-acetylthio-2-azetidinone (36.2 g., 0.250 mole) in 1200 ml. of benzene. The mixture was refluxed for 17 hours in a Dean-Stark apparatus. The solution was concentrated on a rotary evaporator to give the title product as a yellow oil (102 g., 100%). This oil was found to be identical with the product of Example 1A.

B. p-Nitrobenzyl 2-(4-Acetylthio-2-oxo-1-azetidinyl)-2-chloroacetate

To a cooled (−10°) and stirred solution of p-nitrobenzyl 2-(4-acetylthio-2-oxo-1-azetidinyl)-2-hydroxyacetate (102 g., 0.250 mole) in tetrahydrofuran (2000 ml.) were added in succession pyridine (27.1 ml., 0.287 mole) and thionyl chloride (25.2 ml., 0.287 mole); the thionyl chloride addition was done over ca 15 minutes. The mixture was stirred for 30 minutes at −10° and filtered. Concentration of the filtrate left a yellow oil which was partially purified by absorption on a pad of silica gel (800 ml.) and elution with chloroform (ca 3000 ml.). Concentration of the eluates gave an oil (92.9 g., 100%) which was found to contain a minimum of 90% of the title ester as a mixture of epimers.

C. p-Nitrobenzyl 2-(4-acetylthio-2-oxo-1-azetidinyl)-2-triphenylphosphoranylideneacetate To a solution of crude p-nitrobenzyl 2-(4-acetylthio-2-oxo-1-azetidinyl)-2-chloroacetate (92.9 g., 0.249 mole) in dioxane (1200 ml.) were added in succession 2,6-lutidine (31 ml., 0.274 mole) and triphenylphosphine (71.7 g., 0.274 mole). The resulting mixture was stirred at 45°–47° for 18 hours, cooled to 23° and filtered. The filtrate was concentrated on a rotary evaporator to leave a yellow oil which was purified as follows: absorption on a column of silica gel[1] and elution with petroleum ether (4000 ml.), methylene chloride (4000 ml.) and ethyl acetate (4000 ml.).

[1] 100 ml. of Mallinkrodt No. 2847 Silicic Acid, 100 mesh, and 1000 ml. of BDH No. 7734 (E. M. Reagents) Silica Gel 60, 70–230 mesh.

The petroleum-ether fraction was discarded since it contained only impurities. The ethyl acetate fraction was concentrated on a rotary evaporator and the oily residue was triturated with diethyl ether to give the title product as a white solid (74.5 g.), m.p. 162°–165°. The methylene chloride eluate was concentrated to dryness and the oily residue again purified by chromatography as above to give 15.0 g. of title product. The combined solids were dissolved in methylene chloride, treated with activated charcoal, concentrated and recrystallized in diethyl ether to give a total of 87 g. (58%) of title product.

Anal. Calc'd for $C_{32}H_{27}N_2O_6PS$: C, 64.20; H, 4.54; N, 4.68; S, 5.35. Found: C, 63.81; H, 4.55; N, 4.68; S, 6.86.

D. p-Nitrobenzyl 2-Methylpenem-3-carboxylate

A solution of p-nitrobenzyl 2-(4-acetylthio-2-oxo-1-azetidinyl)-2-triphenylphosphoranylideneacetate (38.6 g.) in toluene (500 ml.) was kept at reflux temperature for 3.5 hours. Concentration left a semi-solid which was purified by absorption on silica gel[1] (700 ml.) and elution with methylene chloride. The pertinent fractions were combined and concentrated and the residue triturated in diethyl ether to give the title product as a yellow crystalline solid, m.p. 125°–180° (15.0 g., 73%).
[1]500 ml. of Mallinkdrodt No. 2847 Silicic Acid, 100 mesh, and 200 ml. of BDH No. 7734 Silica Gel 60 (E. M. Reagents), 70–230 mesh.

EXAMPLE 3

Sodium 2-Methylpenem-3-carboxylate

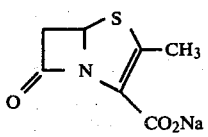

A mixture of p-nitrobenzyl 2-methylpenem-3-carboxylate (512 mg., 1.6 mmole), sodium bicarbonate (134 mg., 1.6 mmole), ethyl acetate (85 ml.), water (40 ml.) and palladium on charcoal (10%, 150 mg.) was hydrogenated in the Parr shaker at an initial pressure of 30 p.s.i. of hydrogen. After 3 hours the catalyst was removed by filtration over Celite (diatomaceous earth). The aqueous phase was decanted and lyophilized to give a white solid, 199 mg. (60% yield). The solid was determined to be a mixture of 80% title product and 20% sodium acetate. $\nu_{c=o}=1765$, 1610, 1580; $\lambda_{max}=258$ ($\epsilon=1990$), 299 ($\epsilon=2136$). (H$_2$O) $\delta$(ppm, D$_2$O): 5.71 (1H, m, H-5), 3.60 (2H, m, H-6), 2.27 (3H, s, CH$_3$), 1.92 (s, CH$_3$CO$_2$Na).

EXAMPLE 4

Sodium 2-Methylpenem-3-carboxylate

A two-phase mixture made of p-nitrobenzyl 2-methylpenem-3-carboxylate (102 mg., 0.319 mmole) in tetrahydrofuran (9 ml.), diethyl ether (14 ml.) and NaHCO$_3$ (27 mg., 0.321 mmole) in water (7 ml.) was hydrogenated over 30% Pd on Celite (diatomaceous earth) (110 mg.) in a Parr shaker at 30 p.s.i. H$_2$ for 2.5 hours. The catalyst was removed by filtration and the aqueous phase was washed twice with diethyl ether. Lyophilization of the aqueous solution gave the title salt as a yellowish powder (68 mg., hydrated). $\delta$(ppm D$_2$O): 5.67 (1H, dd, J$_{5-6\ cis}$=4, J$_{5-6\ trans}$=2, H-5), 3.82 (1H, dd, J$_{gem}$=17, J$_{6-5\ cis}$=4, H-6), 3.41 (1H, dd, J$_{gem}$=17, J$_{6-5\ trans}$=2, H-6), 2.27 (3H, s, CH$_3$). UV(H$_2$O) $\lambda_{max}$ 297.5 ($\epsilon=2800$), 257 ($\epsilon=2900$).

Substitution of an equivalent weight of KHCO$_3$ in the above produce for the NaHCO$_3$ used therein gives d,l-potassium 2-methylpenem-3-carboxylate.

EXAMPLE 5

2-Methylpenem-3-carboxylic Acid

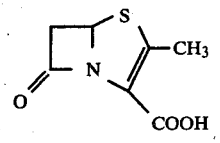

A mixture of p-nitrobenzyl 2-methylpenem-3-carboxylate (305.5 mg., 0.954 mmoles) in tetrahydrofuran (27 ml.), diethyl ether (42 ml.) and NaHCO$_3$ (81 mg., 0.964 mmole) in water (20 ml.) was hydrogenated with 30% Pd on Celite (330 mg.) for 3 hours at 30 p.s.i. H$_2$ on a Parr shaker. The catalyst was removed by filtration and the aqueous phase was washed twice with diethyl ether. The aqueous layer was carefully acidified (pH 2–2.5) with cold 1% HCl and extracted with ethyl acetate (10×20 ml.). The organic extracts were combined, washed three times with brine and dried over Na$_2$SO$_4$. Solvent evaporation afforded a crystalline material which was triturated with diethyl ether to give the title acid (105.8 mg., 60%, decomp. 134° C.). $\delta$(ppm, DMSOd$_6$): 5.64 (1H, dd, J$_{5-6\ cis}$=4, J$_{5-6\ trans}$=2, H-5), 3.82 (1H, dd, J$_{gem}$=16.5, J$_{6-5\ cis}$=4, H-6), 3.37 (1H, dd, J$_{gem}$=16.5, J$_{6-5\ trans}$=2, H-6), 2.28 (3H, s, CH$_3$). $\nu_{c=o}=1795$ and 1775, 1670. UV(EtOH)$\lambda_{max}$ 308 ($\epsilon=6400$), 263 ($\epsilon=4200$).

EXAMPLE 6

Resolution of d,l-2-Methylpenem-3-carboxylic Acid

A. (+)-2-Methylpenem-3-carboxylic Acid

To a suspension of crude d,l-2-methylpenem-3-carboxylic acid (0.925 g., 5 mmole) in isopropanol (10 ml.) was added with stirring d-(+)-α-methylbenzylamine (0.61 g., 5 mmole). The mixture was allowed to stand at room temperature for 0.5 hours. The solid was removed by filtration to give 0.7 g.; [α]$_D$+120.7 (c, 0.058; CHCl$_3$, free acid). This was recrystallized from methanol (6 ml.) to give 0.1 g. of a white solid which was converted to free acid by treatment with cold 1N HCl. Extraction with CHCl$_3$ gave 40 mg. of the title isomer; [α]$_D$+305.6 (c, 0.036, CHCl$_3$). The proton NMR spectrum of the compound was consistent with the expected structure.

B. (−)-2-Methylpenem-3-carboxylic Acid

To a hot solution of crude d,l-2-methylpenem-3-carboxylic acid (1.85 g., 10 mmole) in isopropanol (40 ml.) was added a solution of 1-(−)-α-methylbenzylamine (1.22 g., 10 mmole) in isopropanol (1 ml.). The solution was allowed to crystallize at room temperature for 0.5 hour. The crystalline solid was separated by filtration to give 0.71 g.; [α]$_D$−280.8 (c, 0.12, CHCl$_3$, free acid). The salt was recrystallized from CH$_3$OH (8 ml.) to give 0.27 g. of white solid. This was treated with cold 1N HCl and extracted with CHCl$_3$ to give 0.13 g. of the levorotatory free acid as a white solid, [α]$_D$−304.4 (c, 0.068, CHCl$_3$).

EXAMPLE 7

(+)-Sodium 2-Methylpenem-3-carboxylate

To a solution of (+)-2-methylpenem-3-carboxylic acid in methanol is added one equivalent of sodium ethylhexanoate. There is produced the title salt.

Substitution of potassium ethylhexanoate in the above procedure gives (+)-potassium 2-methylpenem-3-carboxylate.

Treatment of (+)-2-methylpenem-3-carboxylic acid with other pharmaceutically acceptable bases in a suitable solvent gives the corresponding pharmaceutically acceptable carboxylic acid salts.

| | | M.I.C. in meg./ml. | | |
|---|---|---|---|---|
| Organism | | d,l-2-methyl-penem-3-carboxylic acid | d-2-methyl-penem-3-carboxylic acid | l-2-methyl-penem-3-carboxylic acid |
| Str. pneumoniae | A-9585 | 0.03 | 0.06 | 8 |
| Str. pyogenes | A-9604 | 0.13 | 0.25 | 8 |
| Staph. aureus | A-9537 | 0.13 | 0.5 | 32 |
| Staph. aureus and 50% serum | A-9537 | 8 | 4 | >63 |
| Staph. aureus | (Pen-Res) A-9606 | 1 | 0.5 | >125 |
| Staph. aureus | (Meth-Res) A-15097 | 1 | 1 | >125 |
| Str. faecalis | A-20688 | 32 | 32 | 125 |
| E. coli | A-15119 | 8 | 4 | >125 |
| E. coli | A-20341-1 | 16 | 16 | >125 |
| K. pneumoniae | A-15130 | 16 | 8 | >125 |
| K. pneumoniae | A-20468 | >125 | >125 | >125 |
| Pr. mirabilis | A-9900 | 8 | 4 | >125 |
| Pr. vulgaris | A-9716 | 8 | 4 | >125 |
| Pr. morganii | A-15153 | 16 | 8 | >125 |
| Pr. rettgeri | A-21205 | 4 | 4 | >125 |
| Ser. marcescens | A-20019 | 8 | 4 | >125 |
| Ent. cloacae | A-9659 | 16 | 8 | >125 |
| Ent. cloacae | A-9656 | 16 | 8 | >125 |
| Ps. aeruginosa | A-9843A | 125 | 32 | >125 |
| Ps. aeruginosa | A-21213 | >125 | 63 | >125 |

Mouse blood levels of d,l-2-methylpenem-3-carboxylic acid, ampicillin and amoxicillin after oral administration of 100 mg./kg. body weight are shown below:

| | Blood Level (μg./ml.) | | | | | | |
|---|---|---|---|---|---|---|---|
| | 5 | 10 | 15 | 30 | 45 | 60 | 120 |
| Compound | Minutes After Administration | | | | | | |
| d,l-2-Methylpenem-3-carboxylic acid | 28 | 25.1 | 18.4 | <5.6 | <3.9 | <4.3 | <4.3 |
| Ampicillin | 2.1 | 3.9 | 6.1 | 8.2 | 6.1 | 7.9 | 2.8 |
| Amoxicillin | 1.5 | 7.1 | 9.9 | 14 | 15.5 | — | — |

Blood level values represent averages of 4 experiments for d,l-2-methylpenem-3-carboxylic acid, 3 for ampicillin and 1 for amoxicillin.
Assay Organism: *Bacillus megaterium* A-9737

EXAMPLE 8

(+)-Pivaloyloxymethyl 2-Methylpenem-3-carboxylate

A mixture of (+)-2-methylpenem-3-carboxylic acid in dimethylformamide is treated with one equivalent of triethylamine and stirred to effect solution. Bromomethyl pivalate (1 equivalent) in dimethylformamide is then added. The resulting solution is stirred at room temperature. The mixture is then clarified by filtration and the filtrate poured into ice water. The separated solid is filtered, washed with water and dried to give the title ester.

The respective acetoxymethyl, methoxymethyl, acetonyl and phenacyl esters of (+)-2-methylpenem-3-carboxylic acid may be prepared by substituting in the method above for the bromomethyl pivalate used therein an equimolar weight of chloromethyl acetate, chloromethyl methyl ether, chloroacetone and phenacyl bromide, respectively.

Biological Activity Data

The in vitro minimum inhibitory concentrations (MIC) of d,l-2-methylpenem-3-carboxylic acid, (+)-2-methylpenem-3-carboxylic acid and (−)-2-methylpenem-3-carboxylic acid were determined for a number of microorganisms as determined by overnight incubation at 37° C. by tube dilution. Ampicillin was included as a comparison compound. M.I.C. data for the compounds are shown in the following table.

Mouse blood levels of d,l-2-methylpenem-3-carboxylic acid and ampicillin after intramuscular administration of 40 mg./kg. body weight are shown below:

| | Blood Level (μg./ml.) | | | | |
|---|---|---|---|---|---|
| | 5 | 15 | 30 | 45 | 60 |
| Compound | Minutes After Administration | | | | |
| d,l-2-Methylpenem-3-carboxylic acid | 27.1 | 12.7 | <5.9 | <5.9 | <5.9 |
| Ampicillin | 20.8 | 22.8 | 20 | 11.8 | 7.1 |

Blood level values obtained in a single experiment.
Assay Organism: *Bacillus mycoides* A-9528

We claim:
1. A compound of the formula

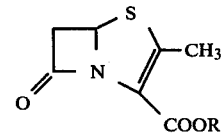

wherein R is hydrogen or an easily removable ester protecting group, or a pharmaceutically acceptable salt thereof.

2. A compound according to claim 1 having the formula

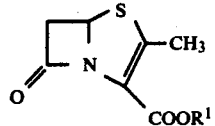

wherein $R^1$ is p-nitrobenzyl or the residue of a physiologically cleavable ester group, said ester being selected from the group consisting of indanyl, phthalidyl, methoxymethyl, glycyloxymethyl, phenylglycyloxymethyl, thienylglycyloxymethyl and acyloxymethyl of the formula

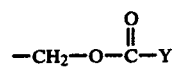

in which Y is $C_1$-$C_4$ alkyl or phenyl.

3. A compound according to claim 2 wherein $R^1$ is p-nitrobenzyl.

4. A compound according to claim 2 wherein $R^1$ is the residue of a physiologically cleavable ester group, said ester being selected from the group consisting of indanyl, phthalidyl, methoxymethyl, glycyloxymethyl, phenylglycyloxymethyl, thienylglycycloxymethyl and acyloxymethyl of the formula

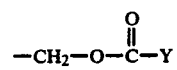

in which Y is $C_1$-$C_4$ alkyl or phenyl.

5. A compound according to claim 2 wherein $R^1$ is indanyl, phthalidyl, methoxymethyl or acyloxymethyl of the formula

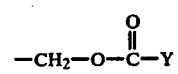

in which Y is $C_1$-$C_4$ alkyl or phenyl.

6. A compound according to claim 2 wherein $R^1$ is methoxymethyl, pivaloyloxymethyl, acetoxymethyl, phthalidyl or indanyl.

7. The acid of claim 1 having the formula

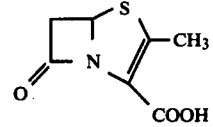

or a pharmaceutically acceptable salt thereof.

8. The acid of claim 7, said acid being 2-methylpenem-3-carboxylic acid.

9. The sodium salt of the acid of claim 7.

10. The potassium salt of the acid of claim 7.

11. The dextrorotatory optical isomer of the compound having the formula

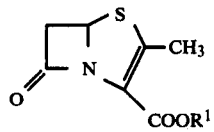

wherein $R^1$ is hydrogen or the residue of a physiologically cleavable ester selected from the group consisting of indanyl, phthalidyl, methoxymethyl, glycyloxymethyl, phenylglycyloxymethyl, thienylglycyloxymethyl and acyloxymethyl of the formula

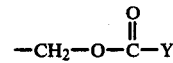

in which Y is $C_1$-$C_4$ alkyl or phenyl or, when $R^1$ is hydrogen, a pharmaceutically acceptable salt thereof, said isomer being substantially free of the corresponding levorotatory optical isomer.

12. The compound of claim 11 wherein $R^1$ is indanyl, phthalidyl, methoxymethyl or acyloxymethyl of the formula

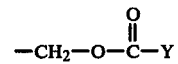

in which Y is $C_1$-$C_4$ alkyl or phenyl.

13. The compound of claim 11 wherein $R^1$ is methoxymethyl, pivaloyloxymethyl, acetoxymethyl, phthalidyl or indanyl.

14. The acid of claim 11 having the formula

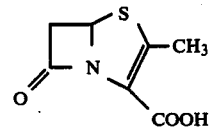

or a pharmaceutically acceptable salt thereof.

15. The acid of claim 11, said acid being (+)-2-methylpenem-3-carboxylic acid.

16. The sodium salt of the acid of claim 11.

17. The potassium salt of the acid of claim 11.

* * * * *

Notice of Adverse Decision in Interference

In Interference No. 100,502, involving Patent No. 4,155,912, M. Menard and G. Caron, 2-METHYLPENEM-3-CARBOXYLIC ACID ANTIBIOTICS, final judgment adverse to the patentees was rendered Feb. 9, 1981, as to claims 1-17.

[*Official Gazette June 2, 1981.*]